(12) United States Patent
Kim

(10) Patent No.: US 9,851,288 B2
(45) Date of Patent: Dec. 26, 2017

(54) EVENT-DRIVEN COULTER COUNTER IC FOR HIGH THROUGHPUT PARTICLE COUNTING

(71) Applicant: Agency for Science, Technology and Research, Singapore (SG)

(72) Inventor: Seong-Jin Kim, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 226 days.

(21) Appl. No.: 14/938,711

(22) Filed: Nov. 11, 2015

(65) Prior Publication Data

US 2016/0139024 A1    May 19, 2016

(30) Foreign Application Priority Data

Nov. 11, 2014    (SG) .......................... 10-2014-07423Q

(51) Int. Cl.
*G01N 27/00*    (2006.01)
*G01N 15/12*    (2006.01)
(Continued)

(52) U.S. Cl.
CPC .... *G01N 15/1227* (2013.01); *B01L 3/502715* (2013.01); *B01L 3/502761* (2013.01); *G01N 15/1056* (2013.01); *G01N 33/48735* (2013.01); *G01N 33/48785* (2013.01); *B01L 2200/0647* (2013.01); *B01L 2300/0645* (2013.01); *G01N 2015/1006* (2013.01); *G01N 2015/1254* (2013.01)

(58) Field of Classification Search
CPC ............ G01N 15/1227; G01N 15/1056; B01L 3/502761; B01L 3/502715
See application file for complete search history.

(56) References Cited

U.S. PATENT DOCUMENTS

2003/0020447 A1*    1/2003    Taylor .................... G01N 15/12
                                                              324/71.4
2009/0011430 A1*    1/2009    Ateya ................ G01N 27/3276
                                                              435/7.2
(Continued)

*Primary Examiner* — Tung X Nguyen
*Assistant Examiner* — Dominic Hawkins
(74) *Attorney, Agent, or Firm* — Intellectual Property Law Group LLP

(57) ABSTRACT

A particle occurrence sensing circuit for microfluidic particle sensing includes a set of particle event indicators, each of which includes: a Coulter counter having a sensing electrode exposable to a fluid within a microfluidic channel and configured for providing a particle sensing signal; an input stage configured for providing an extracted particle sensing signal; and a particle event detector configured for providing a set of particle event occurrence signals. Each of the set of particle event occurrence signals indicates a sensed occurrence of a particle greater than or equal to a given reference particle size during fluid flow through the microfluidic channel to which the sensing electrode is exposed. The particle event detector includes a successive approximation (SA) analog-to-digital converter (ADC) configured for generating a plurality of reference particle size threshold values and successively comparing the extracted particle sensing signal amplitude with reference particle size threshold values.

19 Claims, 11 Drawing Sheets

(51) Int. Cl.
    *B01L 3/00*        (2006.01)
    *G01N 33/487*   (2006.01)
    *G01N 15/10*    (2006.01)

(56) References Cited

U.S. PATENT DOCUMENTS

2011/0279130 A1* 11/2011 Reccius ............. G01N 15/1056
                                                                      324/649
2014/0008307 A1* 1/2014 Guldiken .......... B01L 3/502761
                                                                    210/748.05

* cited by examiner

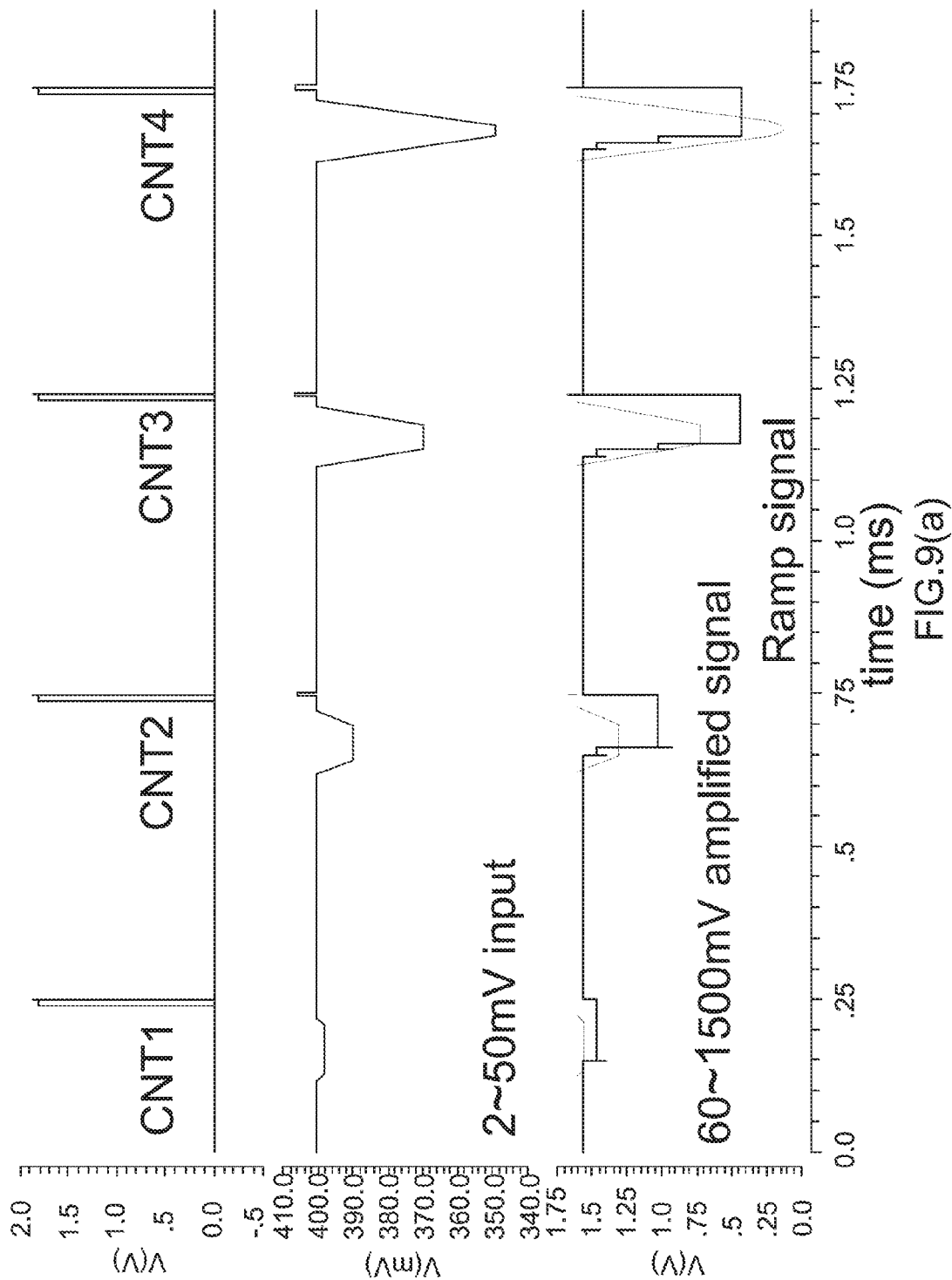

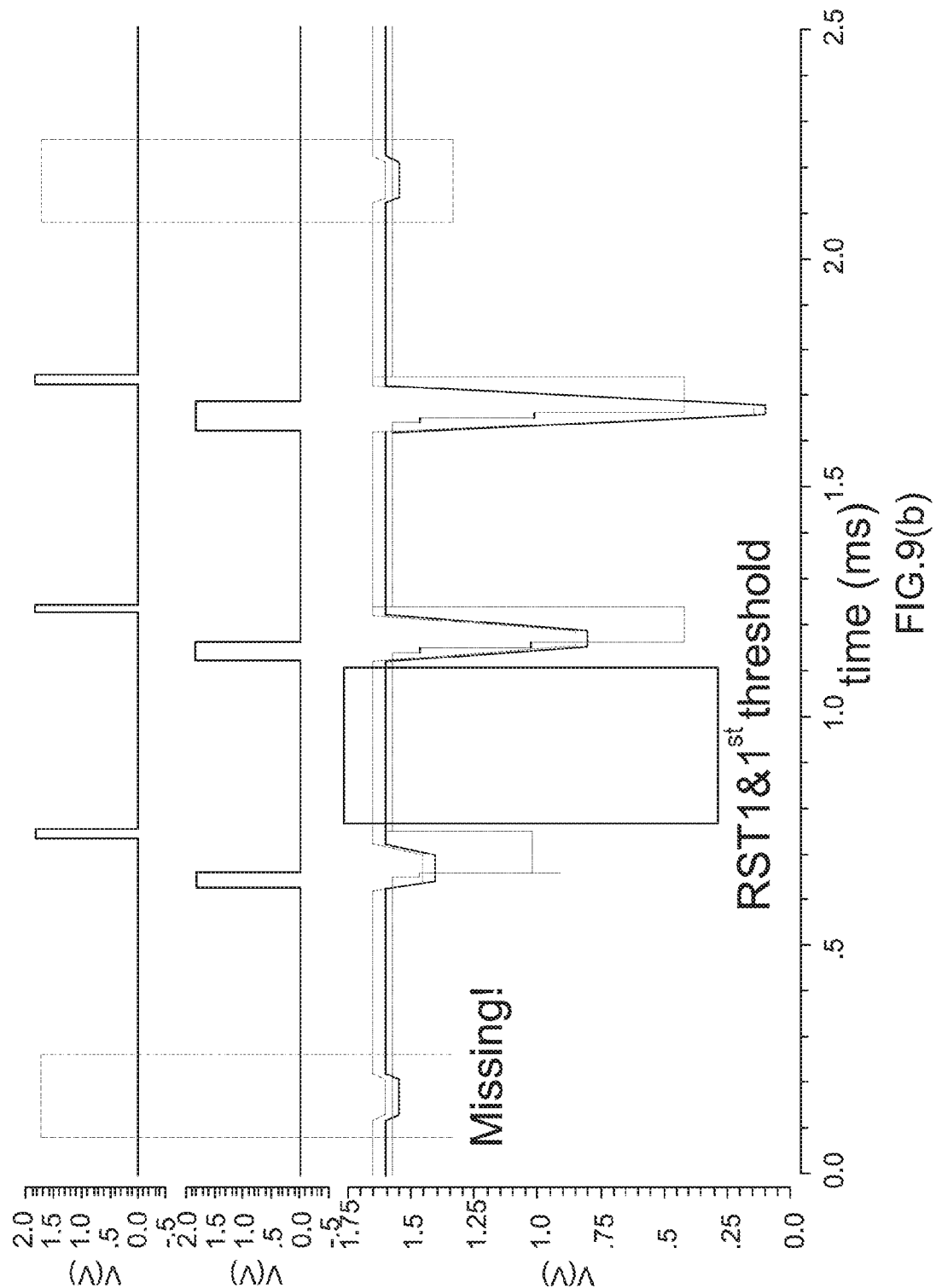

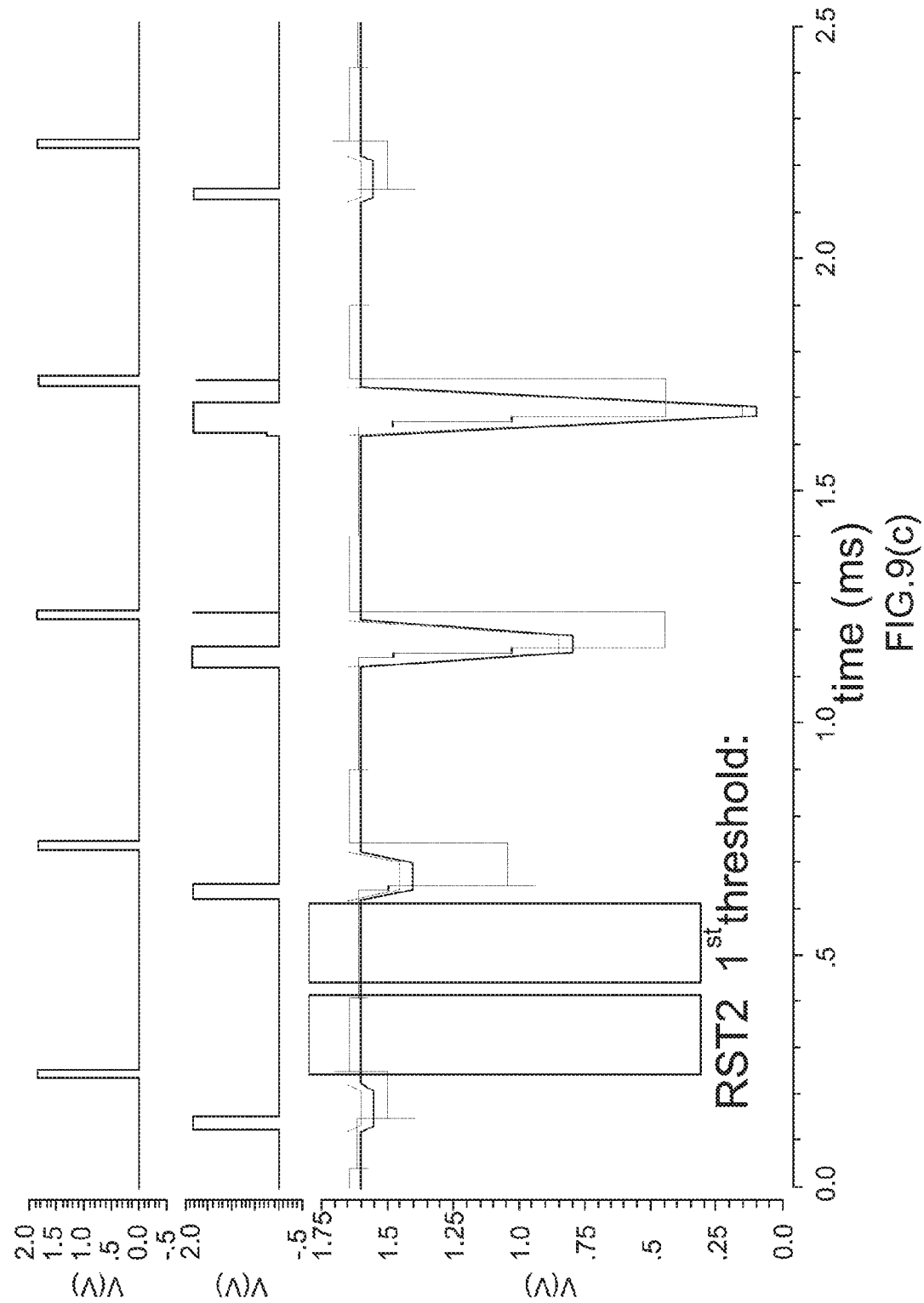

EVENT-DRIVEN COULTER COUNTER IC FOR HIGH THROUGHPUT PARTICLE COUNTING

CROSS-REFERENCE TO RELATED APPLICATION

This application claims priority to Singapore application no. 10201407423Q filed on Nov. 11, 2014, which is hereby incorporated by reference in its entirety.

TECHNICAL FIELD

The present disclosure relates generally to microfluidic flow cytometers, and Coulter counters. Particular aspects of the present disclosure are directed to a high throughput flow cytometer device having a Coulter counter circuit configured for enumerating particles such as biological cells within multiple independently and simultaneously operated microfluidic channels, wherein accumulative particle enumeration or size differentiation for a given microfluidic channel occurs when an amount of potential change in the microfluidic channel exceeds one or more threshold levels.

BACKGROUND

Advances in microelectronics and fluidics technologies in recent years have led to the integration of microfluidic devices and sensors with CMOS circuitry, thereby enabling particular types of point-of-care (POC) devices. A Coulter counter is a promising POC device that can detect the presence of micro-size particles in a fluidic channel based on the Coulter principle involving ionic current modulation within the fluidic channel caused by the presence of the particles (e.g., biological cells) therein. More specifically, a conventional Coulter counter senses or monitors ionic current within an electrolyte present in the fluidic channel, and detects an impedance change when cells are passing through the channel, thereby realizing an electrical flow cytometer or particle/cell counter. Unfortunately, such a conventional particle/cell counter has a lower than desired sensitivity. In an attempt to improve the sensitivity of this type of particle/cell counter, a MOSFET device has been introduced to convert the impedance change to MOSFET drain current modulation in the manner shown in FIG. 1. Although this approach can enhance particle/cell counter sensitivity, it is not suitable for implementing high throughput devices having multiple microfluidic channels because typical MOSFET devices suffer from an undesirable amount of threshold voltage variation.

SUMMARY

A first aspect of the present disclosure provides a circuit for sensing distinct occurrences of particles of one or more sizes (e.g., a first reference particle size, a second reference particle size, a third reference particle size, etc. . . . ) or particles falling within one or more particle size ranges (e.g., a first reference particle size range, a second reference particle size range, a third reference particle size range, etc. . . . ) during flow of at least one fluid in which particles are expected to exist within a set of microfluidic channels, where the circuit can comprise a set of particle event indicators. Each of the particle event indicators can include: a Coulter counter comprising a sensing electrode exposable to a fluid carried within a distinct microfluidic channel of the set of microfluidic channels and configured for providing a particle sensing signal; an input stage configured for receiving the particle sensing signal and providing an extracted particle sensing signal having an amplitude; and a particle event detector configured for receiving the extracted particle sensing signal and providing a set of particle event occurrence signals based upon the extracted particle sensing signal amplitude, wherein each of the set of particle event occurrence signals indicates a sensed occurrence of a particle greater than or equal to a given size (e.g., a given reference particle size) during fluid flow through the microfluidic channel to which the sensing electrode is exposed, and wherein the particle event detector comprises a successive approximation (SA) analog-to-digital converter (ADC) configured for generating a plurality of reference particle size threshold values and successively comparing the extracted particle sensing signal amplitude with reference particle size threshold values.

In some embodiments, the set of particle event occurrence signals can include: a first particle event occurrence signal configured for indicating individual occurrences of particles greater than or equal to a first particle size (e.g., a predetermined first reference particle size of interest); and a second particle event occurrence signal configured for indicating individual occurrences of particles greater than or equal to a second particle size (e.g., a predetermined second reference particle size of interest). The first particle size and the second particle size can be different from each other; for instance, the second particle size can be larger than the first particle size (e.g., the first particle size can correspond to or indicate a smallest particle size of interest/under consideration; and the second particle size can correspond to or indicate a next-larger particle size of interest/under consideration relative to the first particle size).

The first particle event occurrence signal can indicate individual occurrences of particles having a size greater than or equal to the first particle size (e.g., the first reference particle size) as a result of the first particle event occurrence signal being larger than a predetermined first threshold value (e.g., which is correlated with or corresponds to the first reference particle size). The second particle event occurrence signal can indicate individual occurrences of particles having a size greater than or equal to the second particle size (e.g., the second reference particle size) as a result of the second particle event occurrence signal being larger than a predetermined second threshold value (e.g., which is correlated with or corresponds to the second reference particle size).

In various embodiments, each of the plurality of reference particle size threshold values can be adjustable, selectable, or programmably variable.

The SA ADC can include a charge redistribution SA ADC having a plurality of capacitors couplable to a comparator. The SA ADC can further include a ramp generator circuit configured for generating reference particle size threshold values in a sequential stepwise manner. The SA ADC can be configured for selectively transitioning from a current reference particle size threshold value to a successive reference particle size threshold value based upon the extracted particle sensing signal amplitude relative to the current reference particle size threshold value. In some embodiments, the plurality of reference particle size threshold values can include a baseline threshold value established based upon a noise level associated with the particle sensing signal or the extracted particle sensing signal, and/or an inherent voltage offset within the SA ADC.

Each particle event indicator above can further include a set of counters, each counter within the set of counters having an input configured to receive the particle event occurrence signal provided by a distinct particle event output of the particle event detector. In some embodiments, each counter within the set of counters can include a set of outputs at which a binary count value is provided, the binary count value mathematically representing a cumulative count of particles greater than or equal to a particular size (e.g., a particular reference particle size) with respect to a particle event detection interval during which fluid flows through the microfluidic channel to which the sensing electrode is exposed.

In some embodiments, the microfluidic channel that carries the fluid to which the sensing electrode is exposed/exposable includes or is formed by way of a through-hole formed in a substrate material that carries the sensing electrode.

In a number of embodiments, the circuit can include a plurality of particle event indicators, where each of the particle event indicators is configured for operating independently of and simultaneous with each other particle event indicator. Additionally, the set of microfluidic channels can include a plurality of microfluidic channels, each of which is electrically coupled to a distinct particle event indicator (e.g., by way of a sensing electrode).

A second aspect of the present disclosure provides a process for sensing distinct occurrences of particles of one or more sizes (e.g., one or more distinct reference particle sizes) or particles falling within one or more particle size ranges (e.g., one or more distinct reference particle size ranges) during flow of at least one fluid in which particles are expected to exist within a set of microfluidic channels. The process can included: generating a first particle sensing signal by way of a first Coulter counter configured to detect distinct occurrences of particles within a first fluid flowing through a first microfluidic channel; generating a first extracted particle sensing signal from the first particle sensing signal by way of a first input stage circuit; generating a first plurality of reference particle size threshold values; and generating a first set of particle event occurrence signals based upon the amplitude of the first extracted particle sensing signal by successively comparing the first extracted particle sensing signal amplitude with reference particle size threshold values within the first plurality of reference particle size threshold values, wherein each of the particle event occurrence signals within the first set of particle event occurrence signals indicates a sensed occurrence of a particle greater than or equal to a given size (e.g., a given reference particle size) during flow of the first fluid through the first microfluidic channel, and wherein successively comparing the first extracted particle sensing signal amplitude with reference particle size threshold values within the first plurality of reference particle size threshold values occurs by way of a first SA ADC circuit.

The first set of particle event occurrence signals can include: a first particle event occurrence signal configured for indicating individual occurrences of particles greater than or equal to a first particle size (e.g., a first reference particle size) within the first fluid; and a second particle event occurrence signal configured for indicating individual occurrences of particles greater than or equal to a second particle size (e.g., a second reference particle size) within the first fluid. The first particle size and the second particle size can be different from each other, for instance, the second particle size can be larger than the first particle size.

Each of the plurality of reference particle size threshold values within the first plurality of reference particle size threshold values can be adjustable, selectable, or programmably variable.

The first SA ADC can include a charge redistribution SA ADC including a plurality of capacitors couplable to a comparator. The process described above can further include generating reference particle size threshold values within the first plurality of reference particle size threshold values using a ramp generator circuit of the first SA ADC. The process can also include selectively transitioning from a current reference particle size threshold value within the first plurality of reference particle size threshold values to a successive reference particle size threshold value within the first plurality of reference particle size threshold values based upon the first extracted particle sensing signal amplitude relative to the current reference particle size threshold value. The process can further include generating a baseline threshold value corresponding to the first plurality of reference particle size threshold values based upon a noise level associated with the particle sensing signal or the extracted particle sensing signal, and/or an inherent voltage offset within the first SA ADC.

The process described above can additionally include providing each particle event occurrence signal within the first set of particle event occurrence signals to a counter configured for generating a binary count value that mathematically represents a cumulative count of particles greater than or equal to a particular size (e.g., a particular reference particle size) with respect to a particle event detection interval during which the first fluid flows through the first microfluidic channel.

In some embodiments, the process described above can further include: generating a second particle sensing signal by way of a second Coulter counter configured to detect distinct occurrences of particles within a second fluid flowing through a second microfluidic channel; generating a second extracted particle sensing signal from the second particle sensing signal by way of a second input stage circuit; generating a second plurality of reference particle size threshold values; and generating a second set of particle event occurrence signals based upon the amplitude of the second extracted particle sensing signal by successively comparing the second extracted particle sensing signal amplitude with reference particle size threshold values within the second plurality of reference particle size threshold values, wherein each of the particle event occurrence signals within the second set of particle event occurrence signals indicates a sensed occurrence of a particle greater than or equal to a given size (e.g., a given reference particle size) during flow of the second fluid through the second microfluidic channel, and wherein successively comparing the second extracted particle sensing signal amplitude with reference particle size threshold values within the second plurality of reference particle size threshold values occurs by way of a second SA ADC circuit.

In multiple embodiments, generating the second set of particle event occurrence signals can occur in a manner independent of and simultaneous with generating the first set of particle event occurrence signals.

BRIEF DESCRIPTION OF THE DRAWINGS

FIG. 9(a)-9(c) show simulation results for SA ADCs corresponding to open-loop and closed-loop configurations in accordance with embodiments of the present disclosure.

DETAILED DESCRIPTION

The present disclosure references various representative non-limiting embodiments that are provided for purpose of illustration to aid understanding. In the present disclosure, depiction of a given element or consideration or use of a particular element number in a particular FIG. or a reference thereto in corresponding descriptive material can encompass the same, an equivalent, or an analogous element or element number identified in another FIG. or descriptive material associated therewith. The use of "/" in a FIG. or associated text is understood to mean "and/or" unless otherwise indicated. The recitation of a particular numerical value or value range herein is understood to include or be a recitation of an approximate numerical value or value range.

As used herein, the term "set" corresponds to or is defined as a non-empty finite organization of elements that mathematically exhibits a cardinality of at least 1 (i.e., a set as defined herein can correspond to a unit, singlet, or single element set, or a multiple element set), in accordance with known mathematical definitions (for instance, in a manner corresponding to that described in An Introduction to Mathematical Reasoning: Numbers, Sets, and Functions, "Chapter 11: Properties of Finite Sets" (e.g., as indicated on p. 140), by Peter J. Eccles, Cambridge University Press (1998)). In general, an element of a set can include or be a system, an apparatus, a device, a structure, an object, a process, a physical parameter, or a value depending upon the type of set under consideration.

Figure 1:
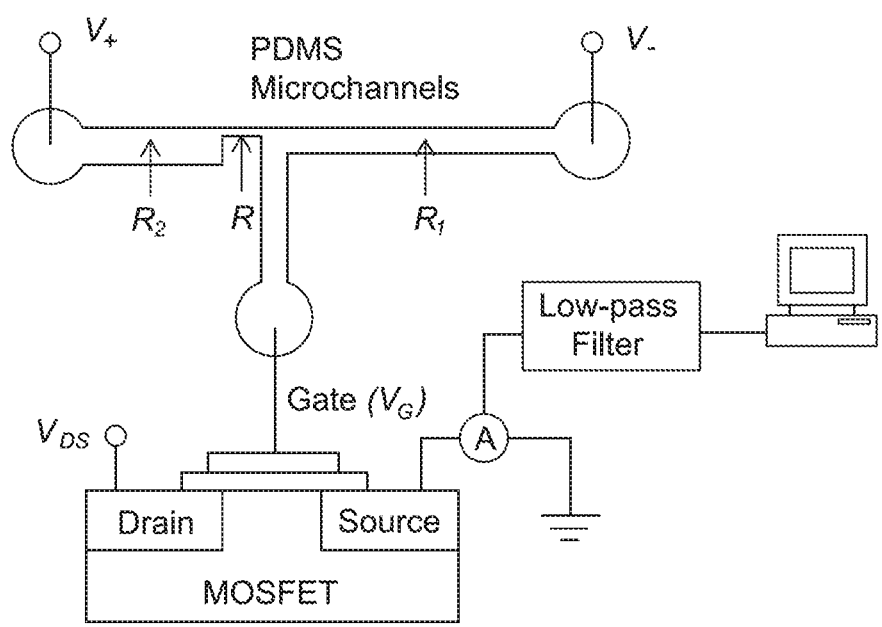
FIG. 1 is a schematic illustration of a prior art Coulter counter circuit that includes a MOSFET for converting impedance changes within a microfluidic channel to MOSFET drain current modulation.
Figure 2:
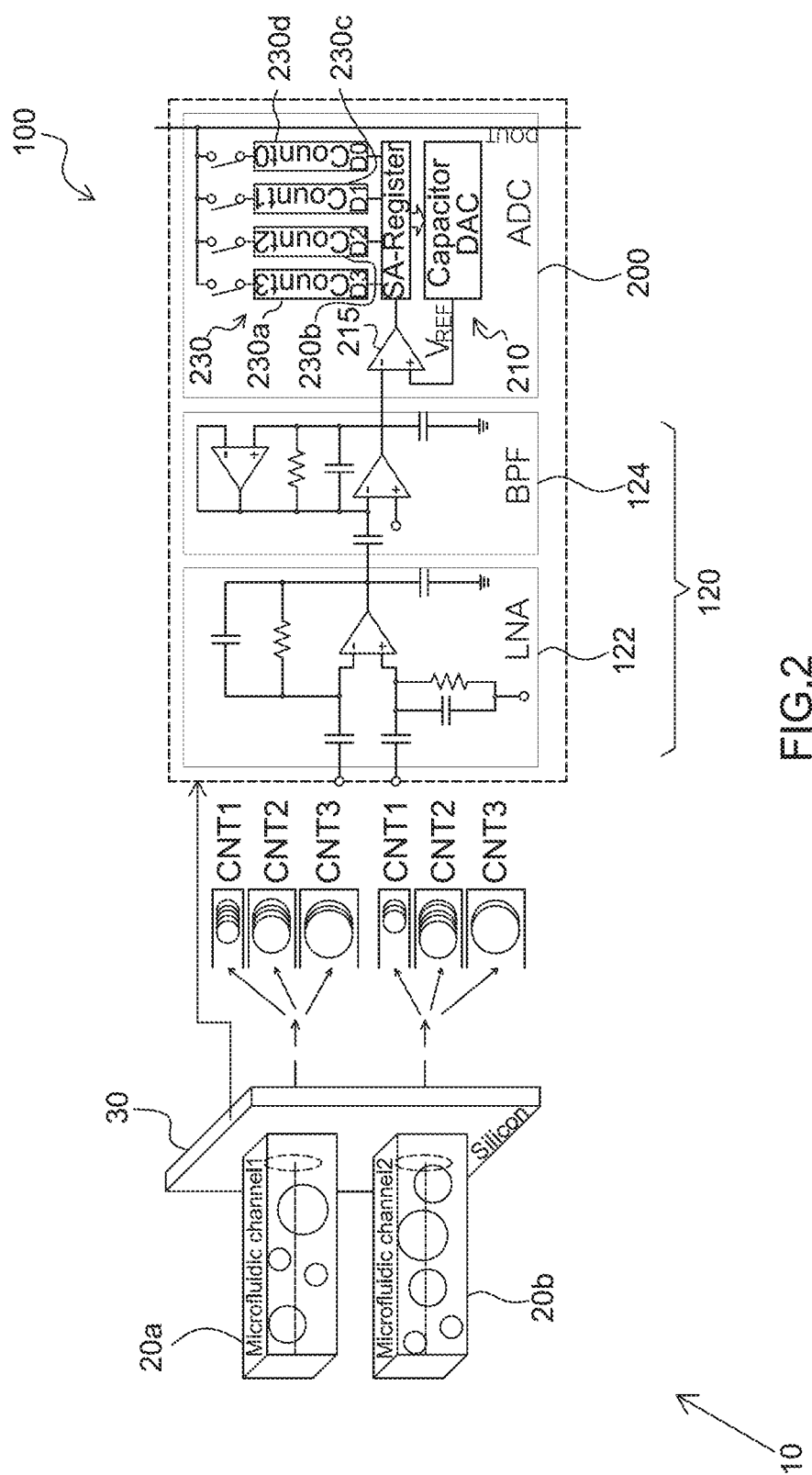
FIG. 2 illustrates portions of a representative microfluidic flow cytometer apparatus or device having a Coulter counter based particle enumeration circuit that includes a set of Successive Approximation (SA) analog-to-digital converters (ADCs) in accordance with an embodiment of the present disclosure.
Figure 3:
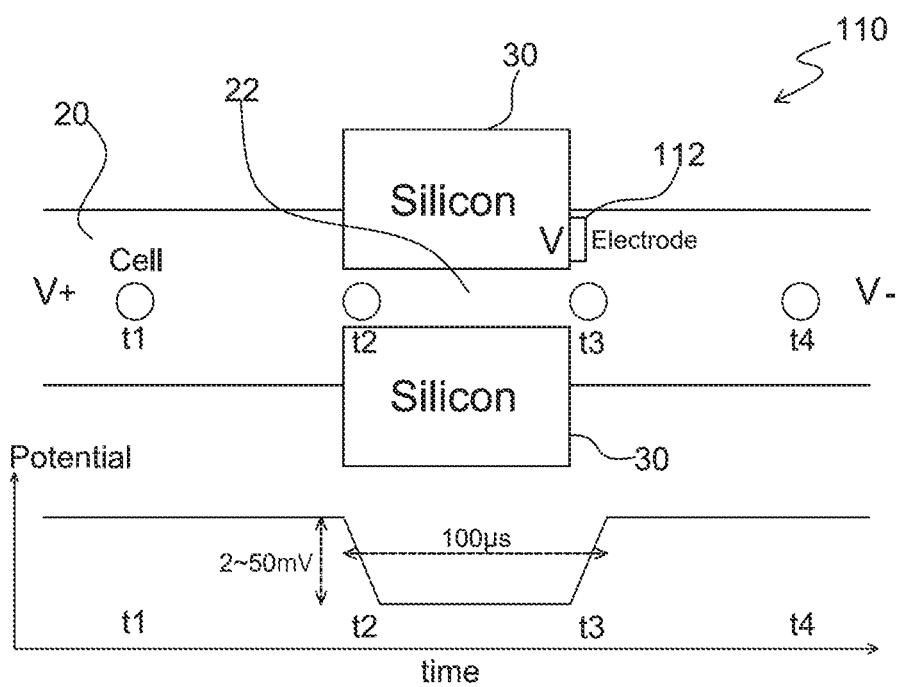
FIG. 3 illustrates portions of a Coulter counter corresponding to a microfluidic channel in accordance with an embodiment of the present disclosure.

FIGS. 2-8 illustrate aspects of a representative microfluidic flow cytometer apparatus or device 10 having a Coulter counter based particle enumeration circuit in accordance with an embodiment of the present disclosure. As shown in FIGS. 2 and 3, the device 10 includes a set of microfluidic channels 20; and a particle event indicator 100 corresponding to each microfluidic channel 20, where each particle event indicator 100 includes, operates in association with, or is based upon a Coulter counter 110. Each particle event indicator 100 is configured for sensing distinct occurrences of particles (e.g., biological cells) of one or more sizes (e.g., relative to a predetermined set of reference particle sizes) or particles falling within one or more particle size ranges (e.g., relative to a predetermined set of reference particle size ranges) during flow of a fluid/electrolyte in which particles are expected to exist within the microfluidic channel 20 to which the particle event indicator 100 corresponds. In several embodiments, the device 10 includes multiple microfluidic channels 20a-b (e.g., two, three, five, ten, twenty, fifty, or more microfluidic channels 20) that are independently and simultaneously operable, and multiple independently and simultaneously operable particle event detectors 100 corresponding thereto. Such a device 10 is configured or configurable for high throughput particle sorting or enumeration for each of its multiple microfluidic channels 20a-b.

In various embodiments, each particle event indicator 100 includes a Coulter counter 110; an input stage 120; and a particle event detector 200. The Coulter counter 110 includes a passage 22 formed as or within a portion of a distinct microfluidic channel 20 to which the particle event indicator 100 corresponds, through which particles can pass; and a sensing electrode 112 exposed or exposable to a fluid carried within the passage 22 of this microfluidic channel 20. The passage 22 can be formed in a substrate or substrate material 30, for instance, a silicon substrate or a silicon die 30 having an aperture or hole (e.g., a through-hole) formed therein/therethrough. A silicon substrate 30 can easily integrate with one or more particle event detectors 100 formed as circuitry thereon (e.g., CMOS integrated circuitry) configured for detecting changes in the electrical potential of the fluid/electrolyte inside the microfluidic channel 20 resulting from the presence or transit of particles through the passage 22 thereof, and differentiating the particles by their size(s) in accordance with embodiments of the present disclosure. A particular manufacturing process for forming the set of microfluidic channels 20, the passage 22 corresponding to each, as well as particular design parameters such as the shape and/or volume of the microfluidic channel 20 and/or the passage 22 can be selected or varied in a manner readily understood by individuals having ordinary skill in the relevant art.

The sensing electrode 112 is configured for providing a particle sensing signal corresponding to or representative of the electrical potential within the microfluidic channel 20 (or passage 22 therein) to which the sensing electrode 112 is exposed. The sensing electrode 112 can be manufactured as a conventional type of electrode structure using conventional types of electrically conductive materials (e.g., one or more deposited metals), in a manner also readily understood by individuals having ordinary skill in the art.

Because the impedance change of the microfluidic channel 20 caused by the presence of the particle therein is determined by the ratio between two volumes, i.e., the volume of the microfluidic channel 20 relative to the volume of the particle therein (or the volume of the passage 22 relative to the volume of the particle therein), the potential change and hence the particle sensing signal depends on the size of the particle as illustrated in FIG. 3. The particle sensing signal provided by the sensing electrode 112 is provided to the input stage 120. Considering several representative design parameters such as the volume of the passage 22 and particles/cells having a diameter from 5 μm to 15 μm, a potential modulation from 2 mV to 50 mV in 100 μs duration is expected. Since the typical variation in threshold voltages of MOSFET devices in modern CMOS processes is more than several millivolts, it is not easy to reliably detect a 2 mV potential change in multiple microfluidic channels 20. Hence, each of the particle event indicators 100 includes an input stage 120. The input stage 120 is configured for receiving the particle sensing signal and providing an extracted particle sensing signal. As shown in FIG. 2, the input stage 120 includes a pre-amplifier 122 and a band-pass filter (BPF) 124.

Figure 4:
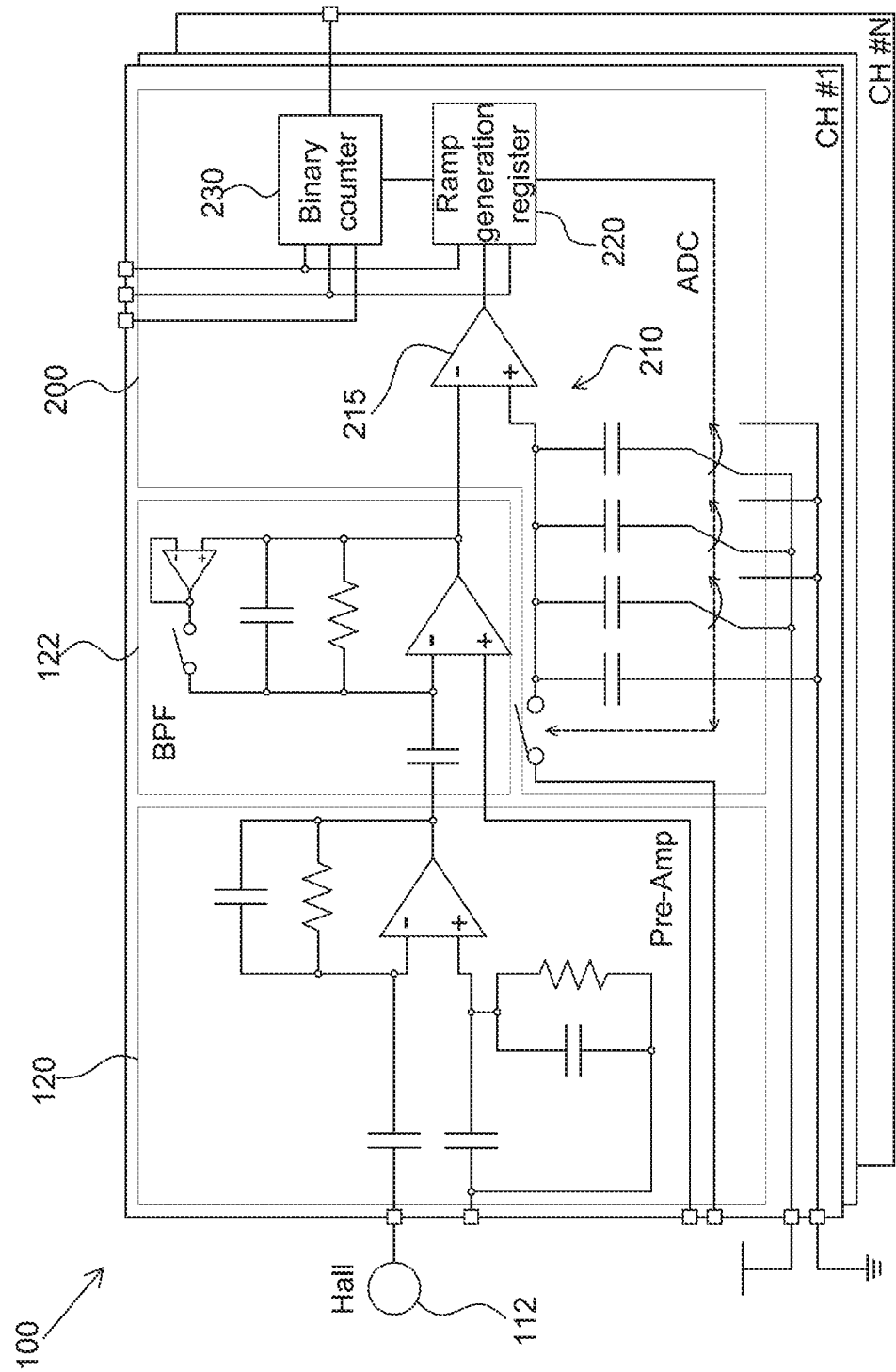
FIG. 4 is a circuit diagram showing a particle event indicator that includes an SA ADC in accordance with an embodiment of the present disclosure.

With further reference to FIG. 4, for a given particle event indicator 100 among one to N particle event indicators 100 corresponding to a total of N particle sensing channels, the sensing electrode 112 thereof exposed to the electrolyte/fluid is coupled to the input stage 120 with a capacitor that decouples the DC signal of the electrolyte/fluid. Hence, the pre-amplifier 122 suppresses potentially large and unknown offset and common mode signals in the sensing electrode and electrolyte interface. The gain of the pre-amplifier 122 is programmable to adjust the size of a feedback capacitor, in a manner readily understood by individuals having ordinary skill in the relevant art. The BPF 124 included in the input stage 120 also provides signal-conditioning capability, rejecting unwanted potential drift and low frequency noise and extracting the signal in the several kHz frequency range that corresponds to or is generated as a result of the presence of the particle within the passage 22 as detected by the sensing electrode 112.

The particle event detector 200 receives the extracted particle sensing signal from the input stage 120, and generates a set of particle event occurrence signals based upon the extracted particle sensing signal amplitude. In various embodiments, each particle event occurrence signal indicates a sensed or detected occurrence of a particle greater than or equal to a given size (e.g., a particular reference particle size of interest or under consideration) during fluid flow through the microfluidic channel 20 to which the sensing electrode 112 is exposed. The particle event detector 200 includes a successive approximation (SA) analog-to-digital (ADC) 210 configured for generating a plurality of reference particle size threshold values and successively comparing the extracted particle sensing signal amplitude with the reference particle size threshold values in order to enumerate or accumulate a count of the number of particles greater than or equal to a particular size (e.g., a given reference particle size, which corresponds to a particular reference particle size threshold value) with respect to a particle event detection interval during which fluid flows through the microfluidic channel 20 to which the sensing electrode 112 is exposed.

Figure 5:
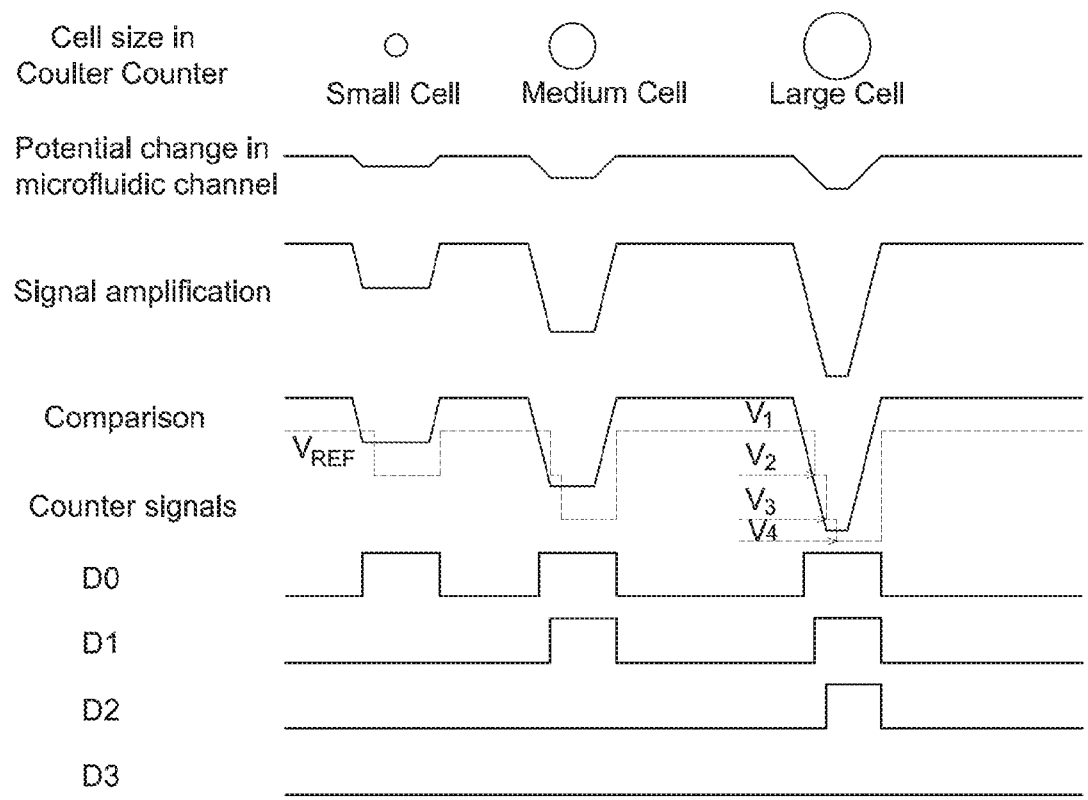
FIG. 5 shows a simplified particle event occurrence diagram corresponding to the detection and enumeration of three differently sized particles (e.g., cells) that travel within a microfluidic channel 20 that is electrically coupled to a particle event indicator in accordance with an embodiment of the present disclosure.

FIG. 5 shows a simplified particle event occurrence diagram corresponding to the detection and enumeration of three differently sized particles (e.g., cells) that travel within a microfluidic channel 20 that is electrically coupled to a particle event indicator 100 in accordance with an embodiment of the present disclosure. The amount of electrical potential change within the microfluidic channel 20 caused by the particle is positively proportional to the particle/cell size as mentioned above, and is amplified and extracted by the input stage 120. FIG. 5 indicates (i) representative particle sensing signals corresponding to electrical potential changes in microfluidic channel 20 sensed by way of a Coulter counter 110; (ii) amplified versions of such particle sensing signals corresponding to representative extracted particle sensing signals generated by an input stage 120; (iii) relative comparison between extracted particle sensing signals and a multi-step ramp signal (e.g., a 4-step ramp signal) generated by a ramp generator circuit 220 of the SA ADC 210 as indicated in FIG. 4, where the multi-step ramp signal is represented as a dotted line in FIG. 5, and each step or increment of the multi-step ramp signal is correlated with or corresponds to a particular particle size (e.g., a particular predetermined reference/threshold particle size); and (iv) four counter signals D0-D3 provided by a counter or set of counters 230 of the particle event detector 200, where the counter 230 includes first through fourth counters 232a-d, and the counter signals D0-D3 have values that are correlated with or correspond to the aforementioned comparison.

In FIG. 5, the "representative potential change in the microfluidic channel" caused by the presence of each differently sized particle is detected by or applied to the sensing electrode 112 (e.g., as each differently sized particle passes through or exits the passage 22 of the microfluidic channel 20 and the electrical potential change within the microfluidic channel 20 caused by the particle is sensed by the sensing electrode 112). This electrical potential change is the particle sensing signal provided to the input stage 120. The representative "signal amplification" in FIG. 5 shows the representative extracted particle sensing signal output from the input stage 120 (which includes the pre-amplifier 122 and the BPF 124). For the "comparison" shown in FIG. 5, the representative dotted-line ramp signal is generated by the ramp generator 220 circuit of the SA ADC 210. The ramp generator circuit 220 can generate reference particle size threshold values in a sequential stepwise manner. The SA ADC 210 selectively transitions from a current reference particle size threshold value to a successive reference particle size threshold value based upon a comparison of the extracted particle sensing signal amplitude or magnitude relative to a current reference particle size threshold value. The comparison between the extracted particle sensing signal amplitude and the reference particle size threshold values is performed by a comparator 215 of the SA ADC 210.

In various embodiments, each reference particle size threshold value is correlated with or corresponds to a particular particle size (e.g., a distinct particle size, such as a predetermined reference particle size). The plurality of reference particle size threshold values typically includes a baseline threshold value established based upon a noise level associated with the particle sensing signal or the extracted particle sensing signal, and/or an inherent voltage offset within the SA ADC 210. The baseline threshold value is set to reject small potential change(s) resulting from noise or inherent voltage offset of the comparator 215 of the SA ADC 210. An extracted particle sensing signal amplitude greater than the baseline threshold value triggers the SA ADC 210 to operate, such that the SA ADC 210 successively generates a set of reference particle size threshold values, e.g., including a first reference particle size threshold value that corresponds to a first reference particle size.

The amplitude of the extracted particle sensing signal is compared with the first reference particle size threshold value. Only when the extracted particle sensing signal amplitude is greater than the first reference particle size threshold value, a next or successive reference particle size threshold value, e.g., a second reference particle size threshold value, is generated by the SA ADC 210 and a first particle event occurrence signal is generated at or provided by a particle event output (e.g., a first particle event output) of the particle event detector 200, indicating an individual occurrence of a particle greater than or equal to the first reference particle size. The first particle event occurrence signal is received by an input of a first counter 232a within the set of counters 230 provided by the particle event detector 200. If the extracted particle sensing signal is less than the first reference particle size threshold value, the operation of the SA ADC 210 terminates or finishes.

Similarly, after the SA ADC 210 generates the second reference particle size threshold value, the extracted sensing signal amplitude is compared with the second reference particle size threshold value. Only when the extracted particle sensing signal amplitude is greater than the second reference particle size threshold value, a next or successive reference particle size threshold value, e.g., a third reference particle size threshold value, is generated by the SA ADC 210 and a second particle event occurrence signal is generated at or provided by a particle event output (e.g., a second particle event output) of the particle event detector 200, indicating an individual occurrence of a particle greater than or equal to a second particle size (e.g., a second reference particle size) correlated with or corresponding to the second reference particle size threshold value. The second particle event occurrence signal is received by an input of a second counter 232d within the set of counters 230 of the particle event detector 200. If the amplitude of the extracted particle sensing signal is less than the second reference particle size threshold value, the operation of the SA ADC 210 terminates or finishes.

Similarly, after the third reference particle size threshold value is generated by the SA ADC 210, the extracted sensing signal amplitude is compared with third reference particle size threshold value. Only when the extracted particle sensing signal amplitude is greater than the third reference particle size threshold value, a next or successive reference particle size threshold value, e.g., a fourth reference particle size threshold value is generated by the SA ADC 210 and a third particle event occurrence signal is generated at or provided by a particle event output (e.g., a third particle event output) of the particle event detector 200, indicating an individual occurrence of a particle greater than or equal to a third particle size (e.g., a third reference particle size) correlated with or corresponding to the third reference particle size threshold value. The third particle event occurrence signal is received by an input of a third counter 232c within the set of counters 230 of the particle event detector 200. If the amplitude of the extracted particle sensing signal is less than the third reference particle size threshold value, the operation of the SA ADC 210 terminates or finishes.

The first particle size, the second particle size, the third particle size can be different from each other. For instance, the third particle size can be larger than the second particle size, and the second particle size can be larger than the first particle size. Each of the plurality of reference particle size threshold values can be adjustable, selectable, or programmably variable.

Depending upon embodiment details and/or the presence or absence of particles of one or more sizes within a microfluidic channel 20, the particle event detector 200 can perform operations that are analogous, similar, or essentially identical to those described above with respect to the successive or sequential generation of additional reference particle size threshold values; successive or sequential comparisons between the extracted particle sensing signal amplitude and each reference particle size threshold value until the amplitude of the extracted particle sensing signal amplitude is less than a current or most-recently generated reference particle size threshold value; and successively or sequentially counting each individual occurrence of when the amplitude of the extracted particle sensing signal is greater than the current or most-recently generated reference particle size threshold value as an occurrence or presence of a particle having a size larger than that of a reference particle size that is correlated with or which corresponds to the current or most-recently generated reference particle size threshold value.

Each counter 232a-d within the set of counters includes a set of outputs, which in various embodiments provides a binary count value. The binary count value mathematically represents a cumulative count of particles greater than or equal to a particular size (e.g., a given reference particle size) with respect to a particle event detection interval during which fluid flows through the microfluidic channel to which the sensing electrode 112 is exposed. After the operation of the SA ADC 210 terminates or finishes as a result of a set of comparison operations as described above, the binary count value of the counter 232 that receives the most-recently generated particle event occurrence signal is incremented by one. The binary count value of each other counter 232 (i.e., each counter that does not receive the most recently generated particle event occurrence signal) of the particle event detector 200 remains unchanged.

The baseline threshold value is important because it is the triggering value or level for operation of the SA ADC 210. Theoretically, the pre-amplifier 122 and BPF 124 can alleviate particular offset, common mode, and low frequency noise signals, but the offset in the amplifier in the BPF 124 and the SA ADC's comparator 215 cannot be removed and may adversely affect pure signal potential. The baseline threshold value should be significantly or very different from each reference particle size threshold value to overcome this problem. However, there is a trade-off between noise immunity and sensitivity because a large baseline threshold level means that the particle event detector 200 cannot reliably detect or enumerate the small potential change generated by a tiny cell. For example, assume that a 3 μm cell leads to an extracted particle sensing signal of 10 mV and the offset of all amplifiers in the circuit is 15 mV. To eliminate the effect of the 15 mV offset, the baseline threshold value should be set to at least 15 mV. Consequently, at least the 3 μm cell cannot be detected. Another solution is to increase the gain in the pre-amplifier and ignore the offset of BPF 124 and the SA ADC. This solution can introduce a voltage headroom problem in the case of large-sized particles such that the power supply voltage should be increased, resulting in large power consumption. In order to solve this problem, the SA ADC 210 can use an offset compensation scheme.

Figure 6A:
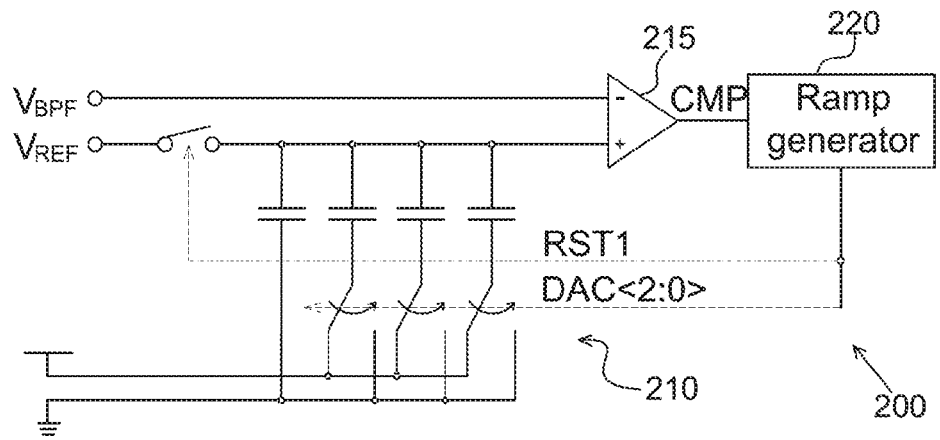
FIG. 6(a) shows portions of an open-loop configuration particle event indicator in accordance with an embodiment of the present disclosure.
Figure 6B:
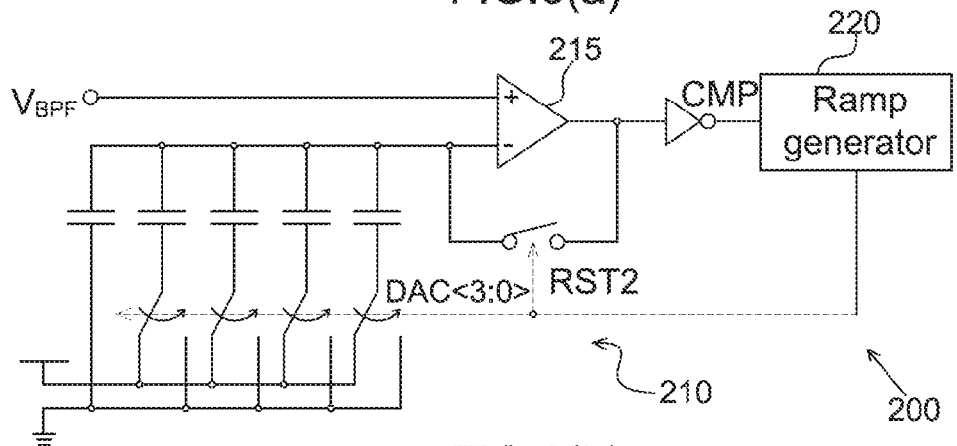
FIG. 6(b) shows portions of a close-loop configuration particle event indicator in accordance with an embodiment of the present disclosure.
Figure 6C:
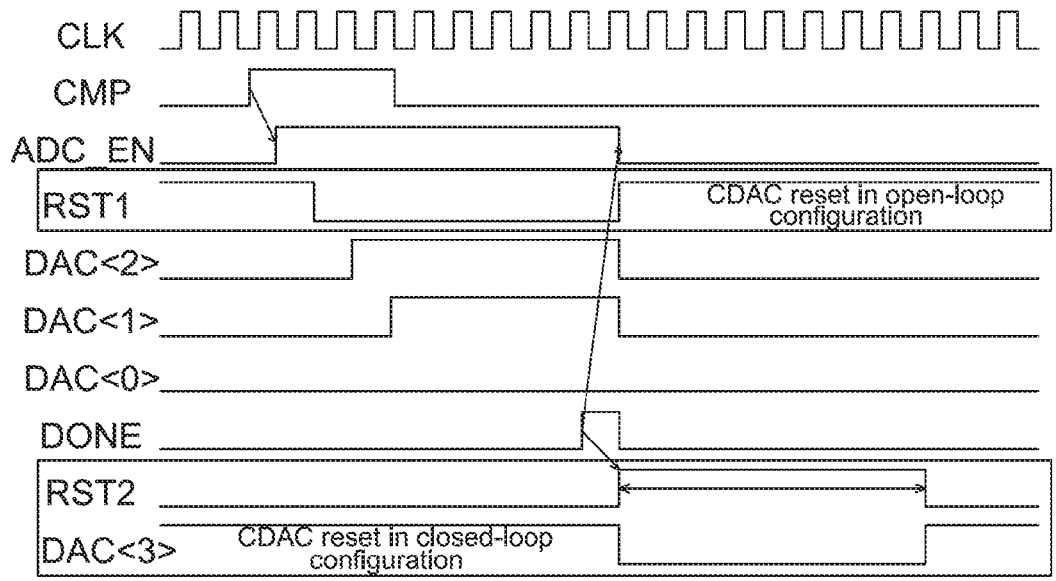
FIG. 6(c) shows a representative timing diagram corresponding to the particle event indicators of FIGS. 6(a) and 6(b).

More particularly, an open-loop particle event indicator configuration in which the baseline threshold value is supplied from an external source is shown in FIG. 6(a). As long as the output of BPF 124, $V_{BPF}$, is higher than the baseline threshold value, CMP and RST1 signals keep low and high, respectively, which implies the reference level ($V_{REF}$) ties to the baseline threshold value supplied by the external source. The offset in $V_{BPF}$ and the comparator 215 is not stored in the open-loop configuration. On the other hand, the offset in $V_{BPF}$ and the comparator 215 can be stored in capacitor- DAC in a closed-loop particle event indicator configuration as shown in FIG. 6(b). After the operation of SA ADC 210 terminates or finishes as indicated by the DONE signal in a timing diagram shown in FIG. 6(c), the comparator 215 is reset by switch RST2 for a period of time as indicated. During this reset, the comparator 215 is configured as a voltage follower and the output level of capacitor DAC is set to $V_{BPF}$ added to offset of the comparator 215. At this moment, all the switches for controlling the capacitor-DAC go high and keep opposite node to VDD. After reset period, one of switches goes low and $V_{REF}$ is changed to the baseline threshold value by charge redistribution. In such an embodiment, this charge redistribution SA ADC 210 includes a plurality of capacitors 212 couplable to the comparator 215 of the SA ADC. As the baseline threshold value is generated from the reset voltage, it includes the offset component. Therefore, the offset can be cancelled by the same operation of the SA ADC 210.

In several embodiments, the device 10 can include a plurality of particle event indicators 100, where each of the particle event indicators 100 is configured or configurable for operating independently of and simultaneous with each other particle event indicator 100. Each particle event indicator 100 corresponds to or is coupled to a distinct microfluidic channel 20 among a plurality of microfluidic channels 20 that are configured or configurable for operating independently of and simultaneous with each other microfluidic channel 20.

The present disclosure provides a process for sensing distinct occurrences of particles of one or more sizes (e.g., relative to one or more reference particular sizes) or particles falling within one or more particle size ranges (e.g., relative to one or more reference particle size ranges) during flow of at least one fluid in which particles are expected to exist within a set of microfluidic channels 20. The process includes: generating a first particle sensing signal by way of a first Coulter counter configured to detect distinct occurrences of particles within a first fluid flowing through a first microfluidic channel; generating a first extracted particle sensing signal from the first particle sensing signal by way of a first input stage circuit; generating a first plurality of reference particle size threshold values (e.g., each of which is correlated with or corresponds to a distinct reference particle size); and generating a first set of particle event occurrence signals based upon the amplitude of the first extracted particle sensing signal by successively comparing the first extracted particle sensing signal amplitude with reference particle size threshold values within the first plurality of reference particle size threshold values, wherein each of the particle event occurrence signals within the first set of particle event occurrence signals indicates a sensed occurrence of a particle greater than or equal to a given size (e.g., a given reference particle size) during flow of the first fluid through the first microfluidic channel, and wherein successively comparing the first extracted particle sensing signal amplitude with one or more reference particle size threshold values within the first plurality of reference particle size threshold values occurs by way of a first SA ADC circuit.

The first set of particle event occurrence signals can include: a first particle event occurrence signal configured for indicating individual occurrences of particles greater than or equal to a first particle size (e.g., a first reference particle size) within the first fluid; and a second particle event occurrence signal configured for indicating individual occurrences of particles greater than or equal to a second particle size (e.g. a second reference particle size) within the first fluid. The first particle size and the second particle size can be different from each other; for instance, the second particle size can be larger than the first particle size. Each of the plurality of reference particle size threshold values within the first plurality of reference particle size threshold values can be adjustable, selectable, or programmably variable.

The process can further comprise generating or providing reference particle size threshold values within the first plurality of reference particle size threshold values using a ramp generator circuit of the first SA ADC. The process can also include selectively transitioning from a current reference particle size threshold value within the first plurality of reference particle size threshold values to a successive reference particle size threshold value within the first plurality of reference particle size threshold values based upon the first extracted particle sensing signal amplitude relative to the current reference particle size threshold value. The process can additionally include comprise generating or providing a first baseline threshold value corresponding to the first plurality of reference particle size threshold values based upon a noise level associated with the particle sensing signal or the extracted particle sensing signal, and/or an inherent voltage offset within the first SA ADC.

The process can also include providing each particle event occurrence signal within the first set of particle event occurrence signals to a first counter configured for generating at least one count value (e.g., a binary count value), where each count value is mathematically correlated with or which mathematically represents a cumulative count of particles greater than or equal to a particular size (e.g., a particular reference particle size) with respect to a first particle event detection interval during which the first fluid flows through the first microfluidic channel.

The process can further include: generating a second particle sensing signal by way of a second Coulter counter configured to detect distinct occurrences of particles within a second fluid flowing through a second microfluidic channel that is distinct from the first microfluidic channel; generating a second extracted particle sensing signal from the second particle sensing signal by way of a second input stage circuit; generating a second plurality of reference particle size threshold values; and generating a second set of particle event occurrence signals based upon the amplitude of the second extracted particle sensing signal by successively comparing the second extracted particle sensing signal amplitude with reference particle size threshold values within the second plurality of reference particle size threshold values, wherein each of the particle event occurrence signals within the second set of particle event occurrence signals indicates a sensed occurrence of a particle greater than or equal to a given size (e.g., a given reference particle size) during flow of the second fluid through the second microfluidic channel, and wherein successively comparing the second extracted particle sensing signal amplitude with one or more reference particle size threshold values within the second plurality of reference particle size threshold values occurs by way of a second SA ADC circuit.

The process can additionally include generating or providing reference particle size threshold values within the second plurality of reference particle size threshold values using a ramp generator circuit of the second SA ADC. The process can also include selectively transitioning from a current reference particle size threshold value within the second plurality of reference particle size threshold values to a successive reference particle size threshold value within the second plurality of reference particle size threshold values based upon the second extracted particle sensing signal amplitude relative to the current reference particle size threshold value. Moreover, the process can include generating or providing a second baseline threshold value corresponding to the second plurality of reference particle size threshold values based upon a noise level associated with the particle sensing signal or the extracted particle sensing signal, and/or an inherent voltage offset within the second SA ADC.

The process can also include providing each particle event occurrence signal within the second set of particle event occurrence signals to a second counter configured for generating at least one count value (e.g., a binary count value), where each count value is mathematically correlated with or which mathematically represents a cumulative count of particles greater than or equal to a particular size (e.g., a particular reference particle size) with respect to a second particle event detection interval during which the second fluid flows through the second microfluidic channel.

Generating the second set of particle event occurrence signals can occur in a manner independent of and simultaneous with generating the first set of particle event occurrence signals. Based upon the description herein, individuals having ordinary skill in the relevant art will understand that the process can be scaled or extended to or across more than two operable particle event indicators 100 configured for independently and simultaneously enumerating particles of particular sizes (e.g., relative to a set of reference particle size threshold values for each particle event indicator) detected within more than two corresponding independently and simultaneously operable microfluidic channels 20.

Figure 7:
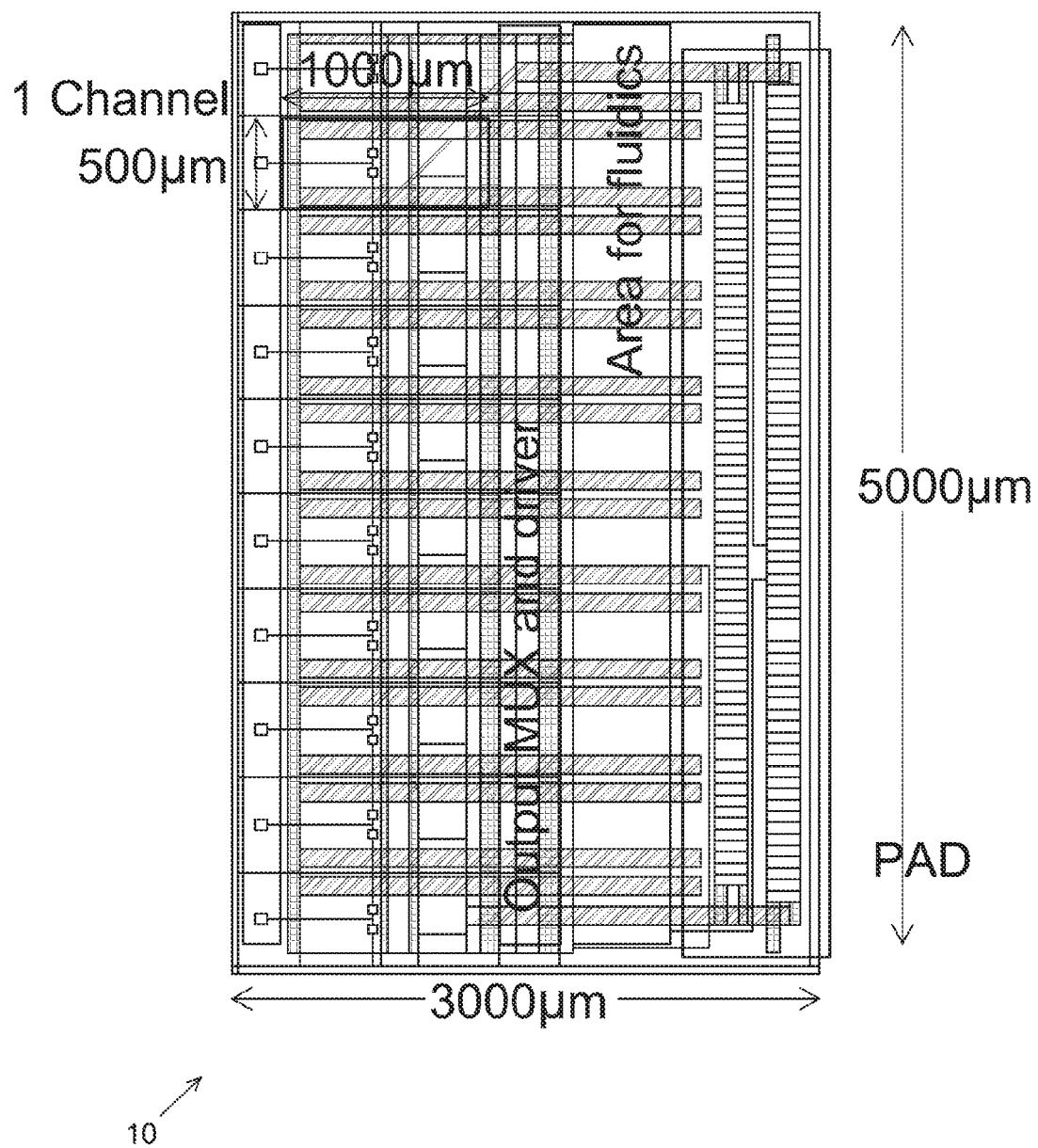
FIG. 7 shows a representative chip layout corresponding to a representative microfluidic flow cytometer apparatus or device having multiple Coulter counter based particle enumeration circuits, including multiple particle event indicators, corresponding to multiple microfluidic channels in accordance with an embodiment of the present disclosure.
Figure 8:
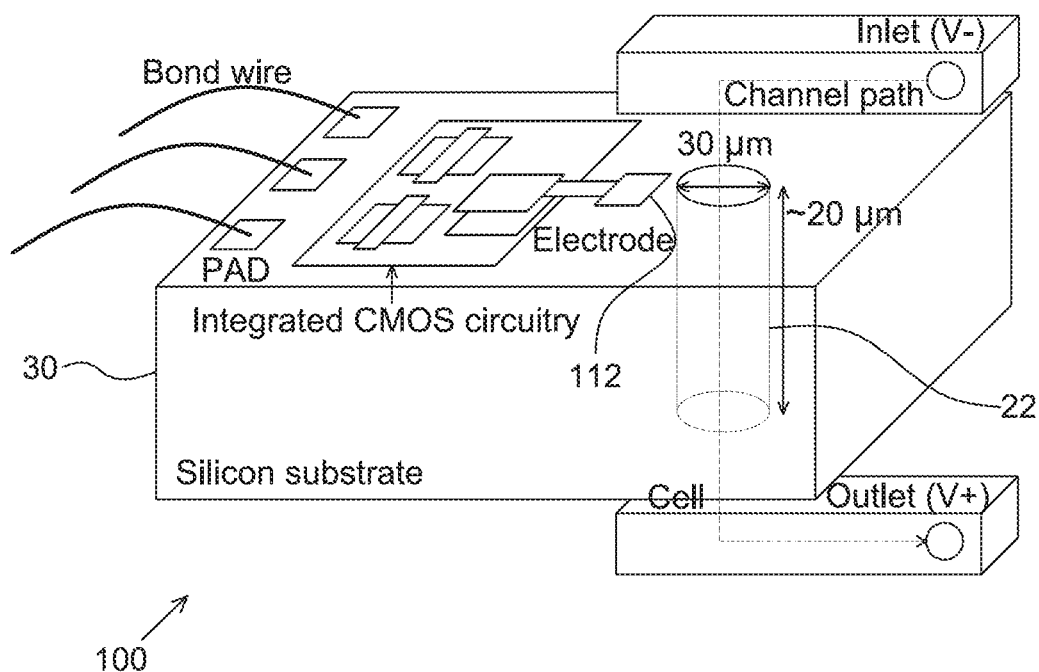
FIG. 8 indicates representative space reserved on a substrate (e.g., a Silicon substrate) for coupling or integrating a microfluidic channel with each Coulter counter based particle enumeration circuit in association with a chip layout such as that shown in FIG. 7.

A device 10 in accordance with an embodiment of present disclosure can be designed using a 1P 6M 0.18 μm CMOS process. FIG. 7 shows a representative example of a corresponding chip layout. The size of the whole chip is 3000 μm×5000 μm, containing 10 counting channels, each of which includes a particle event indicator 100 having a pre-amplifier 122, a BPF 124, and SA ADC 210 incorporated with a through-hole formed in a silicon substrate or die 30. The holes and sensing electrodes 112 are located in left-hand side of the chip in this layout. One circuit occupies less than 500 μm×1000 μm, but a given amount of substrate space (e.g., a significant or large amount of space relative to the aforementioned circuit area) is reserved for the integration of microfluidic channels 20 with device circuitry, for instance, in a manner indicated in FIG. 8. The microfluidic channels 20 can be implemented using PDMS, and can be manually aligned, and hence reserved space is necessary. For performance comparison, both open and closed loop configurations are designed in this chip.

FIGS. 9(a)-9(c) show simulation results with two kinds of SA ADCs 210 corresponding to the open-loop and closed-loop configurations described above. Four different sensing signals, 2, 10, 30, and 50 mV, are applied to the device 10 and the system gain is 30; and CNT1, 2, 3 and 4 represent clock signals for each counter 232a-d corresponding to particle size. Although correct responses can be seen in the open-loop configuration without any offset as shown in FIG. 9(a), the CNT1 signal can be missing when a 50 mV offset is added to the circuitry as indicated in FIG. 9(b). In spite of the 50 mV offset, all CNT signals are correctly generated in the closed-loop configuration as shown in FIG. 9(c). The middle signals in FIGS. 9(b) and 9(c) are the comparator output.

An apparatus/device 10 and circuit/circuitry thereof based on the Coulter principle for high throughput cell sorting is described in accordance with embodiments of the present disclosure. The circuit amplifies potential change caused by the presence of a particle (e.g., a biological cell) in a microfluidic channel 20 into an extracted particle sensing signal so that device/circuit sensitivity can be improved. In addition, each microfluidic channel 20 is electrically coupled to its own successive approximation (SA) analog-to-digital converter (ADC) that compares the extracted particle sensing signal to several reference particle size threshold values and discriminates cells by their size. SA ADC only accumulates each counting register by one when the amount of extracted particle sensing signal exceeds the corresponding reference particle size threshold values. Therefore, the proposed counter enumerates cells passing through a target channel without tracking the potential value of the electrode, eliminating huge memory and reducing power dissipation. It also enables multiple microfluidic channels 20 to be operated independently and simultaneously, realizing high throughput particle enumeration or sorting.

Devices and circuits in accordance with embodiments of the present disclosure enable asynchronous enumeration of particles in each of multiple microfluidic channels 20, which implies or means that the potential of the sensing electrode 112 corresponding to each of the microfluidic channels is not or need not be periodically read out. The counting is operated only when a cell is passing through, thereby optimizing system bandwidth and reducing power consumption.

A prototype integrate circuit has been designed and all functionalities have been successfully verified by simulation. An embodiment in accordance with the present disclosure can be a good candidate for a POC device directed to cell counting and sorting.

What is claimed is:
1. A circuit for sensing distinct occurrences of particles of one or more sizes or particles falling within one or more particle size ranges during flow of at least one fluid in which particles are expected to exist within a set of microfluidic channels, the circuit including a set of particle event indicators, each of the particle event indicators comprising:
a Coulter counter comprising a sensing electrode exposable to a fluid carried within a distinct microfluidic channel of the set of microfluidic channels and configured for providing a particle sensing signal;
an input stage configured for receiving the particle sensing signal and providing an extracted particle sensing signal having an amplitude; and
a particle event detector configured for receiving the extracted particle sensing signal and providing a set of particle event occurrence signals based upon the extracted particle sensing signal amplitude,
wherein each of the set of particle event occurrence signals indicates a sensed occurrence of a particle greater than or equal to a given reference particle size during fluid flow through the microfluidic channel to which the sensing electrode is exposed, and
wherein the particle event detector comprises a successive approximation (SA) analog-to-digital converter (ADC) configured for generating a plurality of reference particle size threshold values and successively comparing the extracted particle sensing signal amplitude with reference particle size threshold values.

2. The circuit of claim 1, wherein the set of particle event occurrence signals includes:
a first particle event occurrence signal configured for indicating individual occurrences of particles greater than or equal to a first reference particle size; and
a second particle event occurrence signal configured for indicating individual occurrences of particles greater than or equal to a second reference particle size,
wherein the first reference particle size and the second reference particle size are different from each other.

3. The circuit of claim 2, wherein the second reference particle size is larger than the first reference particle size.

4. The circuit of claim 1, wherein each of the plurality of reference particle size threshold values is adjustable, selectable, or programmably variable.

5. The circuit of claim 1, wherein the SA ADC comprises:
a charge redistribution SA ADC including a plurality of capacitors couplable to a comparator; and
a ramp generator circuit configured for generating reference particle size threshold values in a sequential stepwise manner.

6. The circuit of claim 5, wherein the SA ADC is configured for selectively transitioning from a current reference particle size threshold value to a successive reference particle size threshold value based upon the extracted particle sensing signal amplitude relative to the current reference particle size threshold value, and wherein the plurality of reference particle size threshold values includes a baseline threshold value established based upon a noise level associated with the particle sensing signal or the extracted particle sensing signal, and/or an inherent voltage offset within the SA ADC.

7. The circuit of claim 1, wherein each particle event indicator further comprises a set of counters, each counter within the set of counters having an input configured to receive the particle event occurrence signal provided by a distinct particle event output of the particle event detector.

8. The circuit of claim 7, wherein each counter within the set of counters includes a set of outputs at which a binary count value is provided, the binary count value mathematically representing a cumulative count of particles greater than or equal to a particular reference particle size with respect to a particle event detection interval during which fluid flows through the microfluidic channel to which the sensing electrode is exposed.

9. The circuit of claim 1, wherein the microfluidic channel that carries the fluid to which the sensing electrode is exposable comprises a through-hole formed in a substrate material that carries the sensing electrode.

10. The circuit of claim 1, wherein the circuit includes a plurality of particle event indicators, and each of the particle event indicators is configured for operating independently of and simultaneous with each other particle event indicator, and wherein the set of microfluidic channels includes a plurality of microfluidic channels.

11. A method for sensing distinct occurrences of particles of one or more sizes or particles falling within one or more particle size ranges during flow of at least one fluid in which particles are expected to exist within a set of microfluidic channels, the method comprising:
generating a first particle sensing signal by way of a first Coulter counter configured to detect distinct occurrences of particles within a first fluid flowing through a first microfluidic channel;
generating a first extracted particle sensing signal from the first particle sensing signal by way of a first input stage circuit;
generating a first plurality of reference particle size threshold values; and
generating a first set of particle event occurrence signals based upon the amplitude of the first extracted particle sensing signal by successively comparing the first extracted particle sensing signal amplitude with reference particle size threshold values within the first plurality of reference particle size threshold values,
wherein each of the particle event occurrence signals within the first set of particle event occurrence signals indicates a sensed occurrence of a particle greater than or equal to a given reference particle size during flow of the first fluid through the first microfluidic channel, and
wherein successively comparing the first extracted particle sensing signal amplitude with reference particle size threshold values within the first plurality of reference particle size threshold values occurs by way of a first SA ADC circuit.

12. The method of claim 11, wherein the first set of particle event occurrence signals includes:
a first particle event occurrence signal configured for indicating individual occurrences of particles greater than or equal to a first reference particle size within the first fluid; and
a second particle event occurrence signal configured for indicating individual occurrences of particles greater than or equal to a second reference particle size within the first fluid,
wherein the first reference particle size and the second reference particle size are different from each other.

13. The method of claim 12, wherein the second reference particle size is larger than the first particle size.

14. The method of claim 11, wherein each of the plurality of reference particle size threshold values within the first plurality of reference particle size threshold values is adjustable, selectable, or programmably variable.

15. The method of claim 11, wherein the first SA ADC comprises a charge redistribution SA ADC including a plurality of capacitors couplable to a comparator, and wherein the method further comprises generating reference particle size threshold values within the first plurality of reference particle size threshold values using a ramp generator circuit of the first SA ADC.

16. The method of claim 15, further comprising:
selectively transitioning from a current reference particle size threshold value within the first plurality of reference particle size threshold values to a successive reference particle size threshold value within the first plurality of reference particle size threshold values based upon the first extracted particle sensing signal amplitude relative to the current reference particle size threshold value; and
generating a baseline threshold value corresponding to the first plurality of reference particle size threshold values based upon a noise level associated with the particle sensing signal or the extracted particle sensing signal, and/or an inherent voltage offset within the first SA ADC.

17. The method of claim 11, further comprising providing each particle event occurrence signal within the first set of particle event occurrence signals to a counter configured for generating a binary count value that mathematically represents a cumulative count of particles greater than or equal to a particular reference particle size with respect to a particle event detection interval during which the first fluid flows through the first microfluidic channel.

18. The method of claim 11, further comprising:
generating a second particle sensing signal by way of a second Coulter counter configured to detect distinct occurrences of particles within a second fluid flowing through a second microfluidic channel;
generating a second extracted particle sensing signal from the second particle sensing signal by way of a second input stage circuit;
generating a second plurality of reference particle size threshold values; and
generating a second set of particle event occurrence signals based upon the amplitude of the second extracted particle sensing signal by successively comparing the second extracted particle sensing signal amplitude with reference particle size threshold values within the second plurality of reference particle size threshold values,
wherein each of the particle event occurrence signals within the second set of particle event occurrence signals indicates a sensed occurrence of a particle greater than or equal to a given reference particle size during flow of the second fluid through the second microfluidic channel, and
wherein successively comparing the second extracted particle sensing signal amplitude with reference particle size threshold values within the second plurality of reference particle size threshold values occurs by way of a second SA ADC circuit.

19. The method of claim 18, wherein generating the second set of particle event occurrence signals occurs in a manner independent of and simultaneous with generating the first set of particle event occurrence signals.

\* \* \* \* \*